(12) United States Patent
Kohan et al.

(10) Patent No.: US 8,044,102 B2
(45) Date of Patent: Oct. 25, 2011

(54) COMPOSITIONS AND METHOD FOR TREATING INFECTION IN CATTLE AND SWINE

(75) Inventors: Raul E. Kohan, New Vernon, NJ (US);
Kanwal J. Varma, Warren, NJ (US);
Robert D. Simmons, Martinsville, NJ (US); Abu Huq, Plainsboro, NJ (US);
Keith A Freehauf, Stockton, NJ (US)

(73) Assignee: Intervet Inc., Summit, NJ (US)

( * ) Notice: Subject to any disclaimer, the term of this patent is extended or adjusted under 35 U.S.C. 154(b) by 843 days.

(21) Appl. No.: 11/206,358

(22) Filed: Aug. 18, 2005

(65) Prior Publication Data

US 2005/0288261 A1      Dec. 29, 2005

Related U.S. Application Data

(63) Continuation of application No. 10/441,392, filed on May 20, 2003, now abandoned.

(60) Provisional application No. 60/382,015, filed on May 20, 2002.

(51) Int. Cl.
*A01N 37/18* (2006.01)
*A01N 43/40* (2006.01)
*A61K 31/165* (2006.01)
*A61K 31/44* (2006.01)

(52) U.S. Cl. .................................. 514/617; 514/352

(58) Field of Classification Search .................. 514/617, 514/352
See application file for complete search history.

(56) References Cited

U.S. PATENT DOCUMENTS

| | | | |
|---|---|---|---|
| 4,733,011 A * | 3/1988 | Riefling et al. ................ | 568/43 |
| 5,082,863 A | 1/1992 | Apelian et al. | |
| 5,242,910 A * | 9/1993 | Damanj ........................ | 514/152 |
| 6,054,434 A | 4/2000 | Kropp et al. | |
| 6,423,298 B2 * | 7/2002 | McNamara et al. ............ | 424/45 |
| 6,787,568 B1 * | 9/2004 | Mihalik ........................ | 514/618 |
| 6,790,867 B2 | 9/2004 | Kohan et al. | |
| 2004/0242546 A1 | 12/2004 | Freehauf et al. | |

FOREIGN PATENT DOCUMENTS

| | | |
|---|---|---|
| EP | 0 980 248 B1 | 2/2000 |
| WO | WO 02/41899 A1 | 5/2002 |

OTHER PUBLICATIONS

Veterinary Pharmaceuticals and Biologicals, VPB 10 Edition, 1997/1998.
D. A. Y. Adawa, et al., "Clinical Trial of Long-Acting Oxytetracycline and Piroxicam in the Treatment of Canine Ehrlichiosis", The Veterinary Quarterly, vol. 14. No. 3, Aug. 1992, pp. 118-120.
I.E. Selman, et. al., "Evaluation of the Efficacy of Flunixin Meglumine Using Four Different Experimentally Induced Bovine Respiratory Disorders", International Symposium on Nonsteroidal Antiinflammatory Agents, Orlando, Florida, Jan. 1986, pp. 23-32.
I. E. Selman, et al., "The effects of Flunixin meglumine and oxytetracycline therapy, alone and in combination, in calves with experimentally-induced pneumonic pasteurellosis", Fourteenth World Congress on Diseases of Cattle, World Association for Buiatrics, vol. 1, (Aug. 1986), pp. 606-610.
J. Deleforge, et al., "A field evaluation of the efficacy of tolfenamic acid and oxytetracycline in the treatment of bovine respiratory disease", J. Vet. Pharmacol. Therap. 17 (1994), pp. 43-47.
Order from *Schering-Plough Ltd.* v. *Norbrook Labs, Ltd.*, HC 05 C00186 (CH. 2005), dated Nov. 25, 2005.
Expert Report of Professor Graham Buckton, submitted in conjunction with the *Schering-Plough Ltd.* v. *Norbrook Labs Ltd.*, HC 05 C00186 (CH. 2005), proceeding.
Expert Report of Professor Jonathan Elliott, submitted in conjunction with the *Schering-Plough Ltd.* v. *Norbrook Labs Ltd.* HC 05 C00186 (CH. 2005), proceeding.
Index to Bundle 2, Statements of Case Orders, from *Schering-Plough Ltd.* v. *Norbrook Labs, Ltd*, HC 05 C00186 (Ch. 2005).
Judgment approved for handing down from *Schering-Plough Ltd* v. *Norbrook Labs Ltd.*, HC 05 C00186 (CH. 2005), dated Nov. 18, 2005.
Copending claims of U.S. Appl. No. 10/857,695, [AH06056US01], pp. 2-5.

\* cited by examiner

*Primary Examiner* — Sreeni Padmanabhan
*Assistant Examiner* — Samira Jean-Louis

(57) ABSTRACT

Novel formulations combining a non-steroidal anti-inflammatory drug (NSAID) such as flunixin, with a fluorinated chloramphenicol or thiamphenicol derivative antibiotic such as florfenicol are disclosed. Methods for using such formulations in the treatment and prevention of infectious diseases of bovines and swine, including bovine respiratory disease and swine respiratory disease, are also disclosed.

1 Claim, 3 Drawing Sheets

COMPOSITIONS AND METHOD FOR TREATING INFECTION IN CATTLE AND SWINE

CROSS-REFERENCE TO RELATED PATENT APPLICATIONS

This patent claims priority as a continuation of U.S. patent application Ser. No. 10/441,392 (filed May 20, 2003; now abandoned), which, in turn, claims benefit of priority to U.S. Provisional Patent Application 60/382,015 (filed May 20, 2002, now expired). The entire text of each of the above-referenced patent applications is incorporated by reference into this patent.

FIELD OF THE INVENTION

The invention relates to compositions and methods for the treatment of infections in animals. More particularly, the invention relates to a composition containing both an antibiotic and a non-steroidal anti-inflammatory drug for use in the treatment of infections in animals such as cattle and swine.

BACKGROUND OF THE INVENTION

All references cited herein are hereby incorporated in their entirety by reference.

Bovine respiratory disease (BRD) occurs in both dairy and beef cattle and is one of the leading causes of economic loss to the cattle industry throughout the world. These economic losses are due to excessive mortality, reduced weight gains as well as treatment and prevention costs. BRD is often referred to as the "bovine respiratory diseases complex" due to the multifactorial etiology.

The cost of death losses due to respiratory diseases vary around the world. Death losses in the U.S. are estimated to approach $1 billion annually. Losses in various European countries range from $75 to $120 million. Cattle with clinical or sub-clinical BRD do not gain weight or produce milk as well as healthy animals. Beef cattle with BRD gain less weight, have reduced feed efficiency and often produce a lower grade carcass at slaughter. Perino L. J., Apley M., *Bovine Respiratory Disease*, in CURRENT VETERINARY THERAPY 4 (FOOD ANIMAL PRACTICE), $4^{TH}$ ED. 446-455 (Howard J. L., Smith R. A., eds., 1999). A direct correlation between pulmonary lesions observed at slaughter and reduced weight gains has been established in cattle with sub-clinical infections. Whittem T. E. et al., *J. Am. Vet. Med. Assoc.*, 209:814-818 (1996).

In addition to the production losses associated with mortality and morbidity, significant costs are associated with the treatment of BRD due to the costs of various therapeutic agents and the labor required to administer these agents, along with the extra labor to isolate and observe these animals.

The pathogenesis of BRD is thought to be due to the interaction of environmental and physiological stresses coupled with infectious agents. *Mannheimia* (*Pasteurella*) *haemolytica, Pasteurella multocida* and *Haemophilus somnus* are considered part of the normal flora of the bovine upper respiratory tract. When environmental and physiological stress factors reduce the natural resistance and inhibit the pulmonary defense mechanisms these organisms proliferate and colonize the lower respiratory tract. In addition, various bovine viruses such as infectious bovine rhinotracheitis virus (IBRV), bovine viral diarrhea virus (BVDV), bovine respiratory syncytial virus (BRSV) and parainfluenza 3 virus (PI-3) are known to have immunosuppressive effects in the lung.

Similarly, swine respiratory disease (SRD) also has a multifactional etiology. Bacterial infections caused by *P. multocida, H. parasuis, Bordetella bronchiseptica, Actinobacillus pleuropneumoniae, Streptococcus suis, Salmonella cholerasuis* and *Mycoplasma* sp. can result in respiratory disease in swine, resulting in significant economic losses. Stresses such as crowding, mixing and moving of pigs and transient viral infections can contribute to the intensification of the disease.

These organisms can stimulate an excessive inflammatory process in the lungs by producing various toxins that stimulate the release of various cytokines, which up-regulate the inflammatory process. *M. haemolytica*, considered the most virulent of these organisms, also produces a leukotoxin that inhibits phagocytosis by leukocytes thus further enhancing its ability to colonize the lower respiratory tract. This process often results in a bacterial bronchopneumonia.

The pulmonary damage that results in death or morbidity is due to the excessive inflammatory response to the invading pathogens. Damage to host tissues occur as neutrophils, pulmonary alveolar macrophages and natural killer cells destroy infected cells. As cell membranes are damaged, arachidonic acid is released. Arachidonic acid is the substrate for the formation of various prostaglandins and other eicosanoids. The release of these biological active substances is critical to driving the inflammatory response that results in pulmonary lesions. Mosier D. A., *Vet. Clin. North Am. Food Animal Prac.*, 13:483-493 (1997).

In general, therapy for BRD should be directed at achieving the following goals:

1. Controlling the infection—In animals where the infectious process is halted early, the need for repeat treatment is significantly reduced (see Apley M. D. & Fajt V. R., *Vet. Clin. North Am. Food Anim. Prac.*, 14:291-313 (1998). The selection of the appropriate antimicrobial compound should be based on the antimicrobial sensitivity of the organism involved, the levels of the antimicrobial agent in the respiratory tract, ease of administration, the potential for injection site tissue damage and a dosing regime that minimizes the pain and stress associated with treatment.

2. Minimize the pulmonary damage—As the level of inflammation and subsequent pulmonary damage increases, the probability of repeat therapy increases and the rate of weight gain decreases. Lekeux P., *Bovine Practitioner*, 29:71-75 (1995); Scott P. R., *J. Dairy Sci.*, 76(2):414-420 (1993).

3. Reduce pyrexia—Controlling the infection and reducing the inflammation will reduce the pyrexia (fever) thus increasing the potential for recovery. The feeling of well-being that accompanies the reduction of pyrexia may also improve the intake of nutrients by suppressing inappetence associated with disease and pyrexia.

For years antimicrobial therapy has been the mainstay of BRD therapy. There are many effective microbial agents currently available for the treatment of BRD. NUFLOR, an injectable formulation of the broad spectrum antibiotic florfenicol, has emerged as one of the leading antibiotics on a global basis. It is indicated for the treatment and control of BRD associated with *M. haemolytica, P. multocida* and *H. somnus* as well as for the prevention of respiratory disease in cattle at high risk of developing BRD associated with these bacteria. NUFLOR is also indicated for the treatment of bovine interdigital phlegmon (footrot, acute interdigital necrobacillosis, infectious pododermatitis) associated with *Fusobacterium necrophorum* and *Bacteroides melaninogenicus*. NUFLOR may be administered subcutaneously as well as intramuscularly.

The pathogenesis of BRD involves the development of a significant inflammatory process in the lungs and the subsequent development of pulmonary lesions, often leading to pulmonary consolidation. The degree of this inflammatory process can determine whether the disease results in mortality, a chronic "poor doer" or the animal recovers uneventfully. Various anti-inflammatory agents have been investigated regarding their ability to reduce the pyrexia, lung consolidation and weight loss associated with BRD.

The use of corticosteroids is generally contraindicated as ancillary therapy for BRD due to their ability to cause serious immunosuppression. The use of non-steroidal anti-inflammatory drugs (NSAIDs) in conjunction with antibiotics, however, has been shown to be of benefit in the treatment of bovine respiratory disease. The nonsteroidal, anti-inflammatory agent flunixin meglumine has been demonstrated to be effective in rapidly reducing pyrexia associated with BRD. Flunixin has also been demonstrated to reduce pulmonary consolidation and the need for re-treatment with antibiotics.

Flunixin meglumine is the active ingredient in FINA-DYNE and BANAMINE (both available from Schering-Plough Animal Health Corporation, Union, N.J.). It has emerged as one of the leading NSAIDs for adjunctive therapy of BRD.

Flunixin meglumine has been studied extensively in regard to its use in conjunction with antibiotics for the treatment of BRD. While it is widely used for this indication, it has not been used in combination in the same formulation with florfenicol because the primary route of administration of flunixin is intravenous and florfenicol is administered intramuscularly or subcutaneously. Moreover, florfenicol formulations have been designed to provide prolonged blood levels of the antibiotic and flunixin would not be expected to have adequate bioavailability in such formulations. In addition, there have been concerns as to whether florfenicol and flunixin would be compatible in such formulations.

Flunixin meglumine has been used in conjunction with oxytetracycline, and products containing both flunixin meglumine and oxytetracycline are commercially available in Europe. However, such combination products require once per day administration for 3 to 5 days. Furthermore, resistance to the antibiotic oxytetracycline has become commonplace in regard to bacterial pathogens, including those commonly associated with BRD.

Accordingly, there is a need for conveniently administered, stable compositions that can control and prevent the infection and minimize the inflammation associated with bovine respiratory disease and other infectious diseases, while minimizing the pain and stress to the animal associated with treatment and the potential for injection site tissue damage.

SUMMARY OF THE INVENTION

The present invention fulfills this need by providing improved compositions and methods for the treatment of bovine respiratory disease and other infections of cattle and swine.

The present invention relates to a composition for the treatment of microbial infection in an animal comprising flunixin or one of its pharmaceutically acceptable salts and a compound of Formula I:

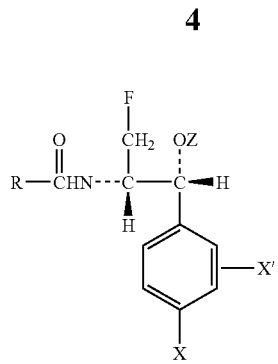

FORMULA I wherein R is a member selected from the group consisting of methyl or ethyl or a halogenated derivative thereof, dihalogenodeuteriomethyl, 1-halogeno-1-deuterioethyl, 1,2-dihalogeno-1-deuterioethyl, azidomethyl and methylsulfonylmethyl;

each of X and X' is a member independently selected from the group consisting of $NO_2$, $SO_2R_1$, $SOR_1$, $SR_1$, $SONH_2$, $SO_2NH_2$, $SONHR_1$, $SO_2NHR_1$, $COR_1$, $OR_1$, $R_1$, CN, halogen, hydrogen, phenyl, and phenyl substituted by halogen, $NO_2$, $R_1$, $PO_2R_1$, $CONHR_1$, $NHR_1$, $NR_1R_2$, $CONR_1R_2$, $OCOR_1$, or $OR_1$, wherein each of $R_1$ and $R_2$ is a member independently selected from the group consisting of methyl, ethyl, n-propyl, isopropyl, butyl, t-butyl, isobutyl and phenyl;

and Z is hydrogen or an acyl group of a hydrocarboncarboxylic acid having up to 16 carbon atoms or an acyl group of an aminohydrocarboncarboxylic acid having up to 12 carbon atoms; and the pharmaceutically acceptable salts of said acyl groups.

In a preferred embodiment, the composition for the treatment of microbial infection in an animal comprises (a) florfenicol; (b) flunixin or one of its pharmaceutically acceptable salts; and (c) from about 5% to about 80% of an aprotic polar solvent.

The present invention also relates to a method of treating a microbial infection in an animal comprising the step of subcutaneously administering to an animal in need of such treatment a therapeutically effective amount of a composition comprising flunixin or one of its pharmaceutically acceptable salts and a compound of Formula I.

In a preferred embodiment, the microbial infection is selected from the group consisting of bovine respiratory disease, swine respiratory disease, footrot, acute mastitis, pinkeye, metritis and enteritis.

The present invention also relates to a method of preventing a microbial infection in an animal susceptible to such an infection comprising the step of subcutaneously administering to an animal susceptible to such an infection a prophylactic amount of a composition comprising flunixin or one of its pharmaceutically acceptable salts and a compound of Formula I.

In a preferred embodiment, the microbial infection is bovine respiratory disease.

DETAILED DESCRIPTION OF THE INVENTION

Figure 1:
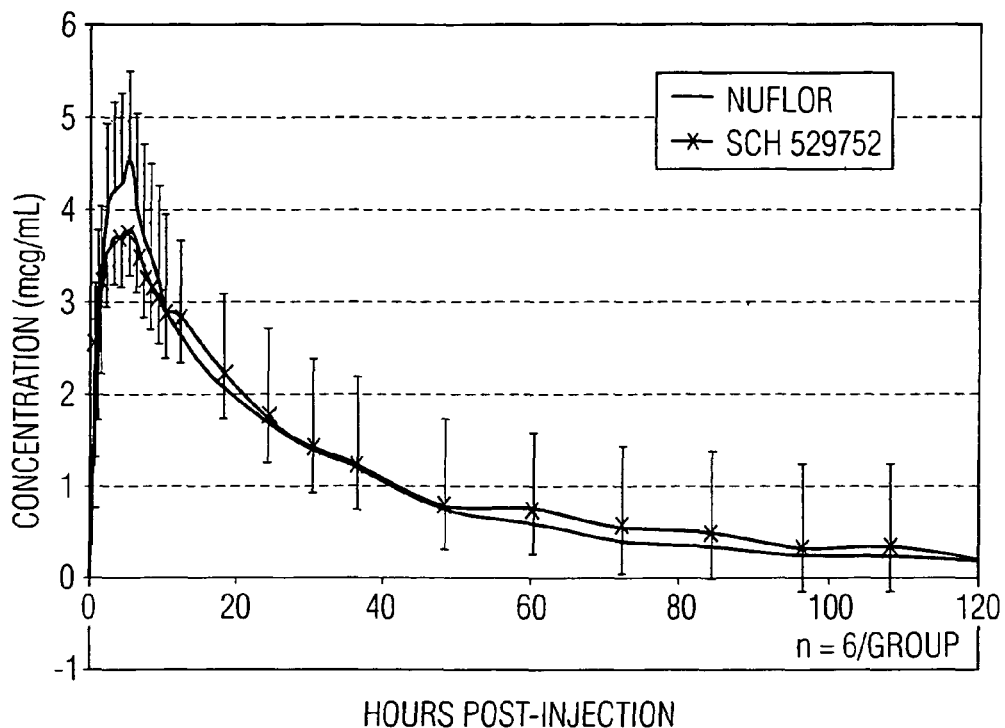
FIG. 1 is a graph showing the mean plasma concentration (+/−SD) of florfenicol vs. time after a single subcutaneous injection of NUFLOR (florfenicol) or a composition of the present invention containing both florfenicol and flunixin meglumine.

When flunixin is administered subcutaneously in a combination formulation with an antibiotic, its bioavailability is significantly reduced. One would expect that this would result in less clinical efficacy when administered in this manner compared to simultaneous administration by the intravenous route.

It has surprisingly been found, however, that, despite the reduced bioavailability of subcutaneously administered flunixin meglumine, the same dose of flunixin meglumine when administered in certain formulations containing a fluorinated chloramphenicol or thiamphenicol analog/derivative antibiotic, is as clinically efficacious as the same amount of flunixin meglumine administered intravenously in conjunction with a separate subcutaneous injection of the antibiotic.

As used herein, the following terms, unless otherwise indicated, shall be understood to have the following meanings:

"Acyl" means an H—C(O)—, alkyl-C(O)—, alkenyl-C(O)—, alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkyl" means an aliphatic hydrocarbon group, which may be straight or branched, comprising from 1 to about 20 carbon atoms in the chain. Preferred alkyl groups contain from 1 to about 12 carbon atoms in the chain. More preferred alkyl groups contain from 1 to about 6 carbon atoms in the chain. Branched means that one or more lower alkyl groups, such as methyl, ethyl or propyl, are attached to a linear alkyl chain. "Lower alkyl" means a group having from 1 to about 6 carbon atoms in the chain, which may be straight or branched. The term "substituted alkyl" means that the alkyl group may be substituted by one or more substituents which may be the same or different.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents," which may be the same or different, and are as defined herein.

"Alkoxy" means an alkyl-O— group in which the alkyl group is as previously described. Non-limiting examples of suitable alkoxy groups include methoxy, ethoxy, isopropoxy, and n-butoxy. The bond to the parent moiety is through the ether oxygen.

"Azido" refers to an —N$_3$ group.

"Halo" and "halogeno" mean fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" and "halogenoalkyl" mean an alkyl group as defined above wherein one or more hydrogen atoms on the alkyl is replaced by a halo group defined above.

"Ring system substituent" means a substituent attached to an aromatic or non-aromatic ring system which, for example, replaces an available hydrogen on the ring system. Ring system substituents may be the same or different.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

An "effective amount" is the dose required to alleviate a particular symptom of an infection or disease or to protect an animal against infections or disease.

As used herein, the term "bovine" refers to animals of the genus *Bos*, such as cattle. The term "bovid" refers to animals in the family Bovidae, which includes hoofed, hollow-horned ruminants such as cattle, sheep, goats, buffaloes, oxen, etc. As used herein, the term "swine" refers to animals of the family Suidae, which includes pigs, boars, warthogs, etc.

Flunixin meglumine is currently approved globally for use in the treatment of BRD. It has become a mainstay of veterinary practice for the treatment of inflammatory conditions. As the veterinarian often administers NSAID therapy with an antibiotic, development of a combination flunixin-antibiotic injectable product would be desirable. Flunixin meglumine is commercially available from, e.g., ISP (Wayne, N.J.), or may be made according to methods known in the art, e.g., the methods described in U.S. Pat. Nos. 3,337,570, 3,478,040 and 3,839,344.

Fluorine-containing analogs of antibiotics chloramphenicol and thiamphenicol have been shown to have antibiotic activity, both against organisms sensitive to and resistant to chloramphenicol and thiamphenicol. See Schafer, T. W. et al., "Novel Fluorine-Containing Analogs of Chloramphenicol and Thiamphenicol: Antibacterial and Biological Properties," in CURRENT CHEMOTHERAPY AND INFECTIOUS DISEASE PROCEEDINGS OF THE 11$^{TH}$ ICC AND THE 19$^{TH}$ ICAAC AMERICAN SOCIETY OF MICROBIOLOGY 1980, 444-446. Examples of such compounds, and methods for their manufacture, are described and claimed in U.S. Pat. No. 4,235,892. The medical profession has become increasingly concerned about the transference of bacterial resistance to humans when antibiotics useful in treating humans are administered to livestock. Because the chloramphenicol group of antibiotics is infrequently used now to treat humans, its derivatives are particularly appropriate for veterinary use. Of particular interest are the 3-fluoro, 3-deoxy derivatives.

The invention provides novel compositions for the treatment of infectious diseases such as bovine respiratory disease in livestock. These compositions are formulations comprising flunixin in combination with certain chloramphenicol derivatives. Initial testing of these formulations demonstrated relatively low serum levels of flunixin in cattle following administration of a single dose. In subsequent clinical trials, the formulations of the present invention demonstrated an unexpected high degree of efficacy when compared to a negative control group as well as a group receiving florfenicol and flunixin concurrently but in separate formulations. The compositions of the present invention comprise flunixin meglumine and at least one antibiotic of Formula I:

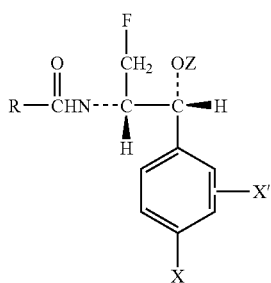

FORMULA I wherein R is a member selected from the group consisting of methyl or ethyl or a halogenated derivative thereof, dihalogenodeuteriomethyl, 1-halogeno-1-deuterioethyl, 1,2-dihalogeno-1-deuterioethyl, azidomethyl and methylsulfonylmethyl;

each of X and X' is a member independently selected from the group consisting of $NO_2$, $SO_2R_1$, $SOR_1$, $SR_1$, $SONH_2$, $SO_2NH_2$, $SONHR_1$, $SO_2NHR_1$, $COR_1$, $OR_1$, $R_1$, CN, halogen, hydrogen, phenyl, and phenyl substituted by halogen, $NO_2$, $R_1$, $OR_1$, $PO_2R_1$, $CONHR_1$, $NHR_1$, $NR_1R_2$, $CONR_1R_2$ or $OCOR_1$, wherein each of $R_1$ and $R_2$ is a member independently selected from the group consisting of methyl, ethyl, n-propyl, isopropyl, butyl, t-butyl, isobutyl and phenyl;

and Z is hydrogen or an acyl group of a hydrocarboncarboxylic acid (preferably a hydrocarbondicarboxylic acid) having up to 16 carbon atoms or an acyl group of an aminohydrocarboncarboxylic acid having up to 12 carbon atoms; and the pharmaceutically acceptable salts of said acyl groups.

Included among the halogenated groups contemplated for the moiety R in Formula I are the mono-, di- and tri-fluoro, the mono-, di- and tri-chloro-, the mono- and di-bromo-, and the iodo-methyl groups as well as the mono- and di-fluoro-, the mono- and di-chloro-, the mono- and di-bromo-, and the iodo-ethyl groups wherein the halogen substituents are preferably on the carbon alpha to the carbonyl function. Also included are mixed dihalogenoalkyl groups in which both halogens are preferably bonded to the carbon alpha to the carbonyl groups, e.g., groups such as fluorochloro-, fluorobromo-, and chlorobromo-methyl and -ethyl, as well as trihalogen-methyl groups such as dichlorofluoro- and difluorochloromethyl.

Also included among the compounds of Formula I are the ester derivatives, e.g. 1-hydrocarboncarboxylates of Formula I wherein Z is an acyl group of a hydrocarboncarboxylic acid having up to 16 carbon atoms that may be saturated, unsaturated, straight chain or branched chain, aliphatic, cyclic, cyclic-aliphatic, aromatic, aryl-aliphatic, or alkyl-aromatic and may be substituted by hydroxy, alkoxy containing from 1 to 5 carbon atoms, carboxyl, $NO_2$, $NHR_1$, $NR_1R_2$, $SR_1$, $SOR_1$, or halogen, wherein $R_1$ and $R_2$ are as defined above.

Other antibacterially active ester derivatives of Formula I are those wherein Z is an acyl group of an amino acid containing up to 12 carbon atoms that may be saturated, unsaturated, straight chain, branched chain or cyclic, that may contain aromatic groups and that may be substituted by hydroxyl groups.

Preferred ester derivatives include those derived from dibasic hydrocarboncarboxylates, e.g. the 1-succinate and 1-palmitate esters, which provide water soluble, pharmaceutically acceptable cationic salts, e.g. the sodium or potassium salts as well as salts with amine, e.g. trimethylamine. Also preferred are ester derivatives of amino acids that provide water soluble, pharmaceutically acceptable acid addition salts with mineral or organic acids, e.g. the hydrochloric, or sulfuric acid, or succinic acid addition salts.

As used herein the term "pharmaceutically acceptable salts" thus includes salts wherein the acidic hydrogen in the dibasic hydrocarboncarboxylate esters of this invention is replaced with a cation (e.g. sodium D-(threo)-1-p-nitrophenyl-2-dichloroacetamido-3-fluoro-1-propyl hemisuccinate) as well as salts wherein the acidic hydrogen forms an acid addition salt with an amine (e.g. D-(threo)-1-p-nitrophenyl-2-dichloroacetamido-3-fluoro-1-propyl hemisuccinate N-trimethylamine salt). Also included are the acid addition salts formed between mineral or organic acids and the amine in the amino acid esters of the compounds of Formula I (e.g. D-(threo)-1-p-nitrophenyl-2-dichloroacetamido-3-fluoro-1-propyl glycinate hydrochloride).

Among the pharmaceutically acceptable cationic salts of the dibasic hydrocarboncarboxylate esters included in Formula I are salts of alkali and alkaline earth metals (e.g., sodium, potassium, calcium, aluminum) and salts with an amine such as trialkylamines, procaine, dibenzylamine, N-benzyl-beta-phenethylamine, N,N'-dibenzylethylenediamine, N-(lower)alkylpiperidines (e.g. N-ethylpiperidine), and N-methyl glucamine.

Preferably R is a halogenated derivative of methyl or ethyl, Z is a hydrogen, X is phenyl, $COR_1$ or $SO_2R_1$, $R_1$ is methyl, and X' is hydrogen. Most preferably R is $CHCl_2$ or $CHF_2$.

A preferred antibiotic compound is florfenicol (D-(threo)-1-p-methylsulfonyl phenyl-2-dichloroacetamido-3-fluoro-1-propanol). Another preferred antibiotic compound is D-(threo)-1-p-methylsulfonyl phenyl-2-difluoroacetamido-3-fluoro-1-propanol. Processes for the manufacture of these preferred antibiotic compounds, and intermediates useful in such processes, are described in U.S. Pat. Nos. 4,311,857; 4,582,918; 4,973,750; 4,876,352; 5,227,494; 4,743,700; 5,567,844; 5,105,009; 5,382,673; 5,352,832; and 5,663,361.

Formulation efforts on the combination product were directed at maintaining the desirable pharmacokinetic profile of florfenicol allowing for one-shot administration to cattle with BRD. A formulation containing 300 mg/mL of florfenicol and 16.5 mg/mL of flunixin, was developed and administered at a dose of 40 mg/kg of florfenicol, and a dose of 2.2 mg/kg of flunixin meglumine. The data presented demonstrated that the bioavailability of florfenicol is unaltered (see FIG. 1). Moreover, the flunixin component acted in a clinically equivalent fashion to that of FINADYNE. In a clinical study in which that formulation was compared to the same formulation with twice as much flunixin and NUFLOR alone, the benefit of flunixin therapy was clearly evident. But no incremental benefit of a higher flunixin dose was apparent (see FIG. 3).

Clinical studies reconfirmed the well-established benefits of flunixin in the treatment of bovine respiratory disease in terms of incremental improvement in clinical response, antipyretic response and decreased lung consolidation. Superiority to antibiotic use alone was evident, particularly in the critical first 24 hours after diagnosis and treatment (see FIGS. 4, 5 and 6).

In addition to greater convenience and ease of use, it is believed that a single daily subcutaneous administration of a combination product in accordance with the present invention will promote humane animal care by reducing the number of injections needed to treat animals and providing more rapid relief of disease symptoms. By reducing the number of injections, manpower costs also may be significantly reduced.

In the formulations of the present invention, the concentration of flunixin typically is from about 1 to about 10% by weight, with the preferred level being at from about 1.5% to about 3.5%, and an even more preferred level being at least about 1.65% by weight. The concentration of florfenicol or other antibiotic typically is from about 10% to about 50% w/v, with the preferred level between about 20% and about 40% w/v, even more preferred being at least about 30% w/v.

The remaining portion of the formulations of the present invention is a pharmaceutically acceptable carrier comprising at least one solvent. The pharmaceutically acceptable carrier comprises from about 40% to about 80% of the formulation.

Florfenicol is generally soluble in aprotic polar solvents such as a pyrrolidone solvent, or N,N-dimethylacetamide, N,N-dimethylformamide, DMSO, acetone or glycerol formal. Preferred pyrrolidone solvents are N-methyl-2-pyrrolidone and 2-pyrrolidone. Accordingly, such an aprotic polar solvent (or a combination of such solvents) is preferred for use in formulations of the present invention that contain florfenicol or similar antibiotics. Preferably such a solvent is present at about 5% to about 80% by weight of the formulation. More preferably such a solvent is present at about 10% to about 35% of the formulation.

Other pharmaceutically acceptable solvents may be present in the formulations of the present invention. Suitable solvents include water, ethanol, isopropanol, 1,2-propanediol, glycerin, benzyl alcohol, dimethylisosorbide, triacetin, glycol ethers, propylene glycol and polyethylene glycol (PEG). Particularly preferred solvents include PEG having an average molecular weight between about 200 and about 400, triacetin, dimethylisosorbide, ethanol, and water, and combinations thereof. These solvents may comprise from 0% to about 75% of the formulation. Preferably they comprise from about 15% to about 60%. More preferably they comprise from about 40% to about 55% of the formulation.

The addition of one or more of such additional solvents may be desirable to reduce the viscosity of the formulation in order to provide a product with workable syringeability. Examples of solvents particularly useful for adjusting the viscosity of the formulations of the present invention include water, ethanol, isopropanol, propylene glycol, dimethylisosorbide and triacetin, and combinations thereof.

Other inert ingredients can be added to the present composition, as desired. Such ingredients include preservatives, chelating agents, antioxidants and stabilizers. Exemplary preservatives include methyl p-hydroxybenzoate (methylparaben) and propyl p-hydroxybenzoate (propylparaben). Exemplary chelating agents include edetate sodium. Exemplary antioxidants include butylated hydroxyanisole and sodium monothioglycerol.

In order to prevent degradation of any of the active ingredients in the formulations of the present invention, the addition of at least one stabilizer has been found to be advantageous. Citric acid is a preferred stabilizer.

In order to prepare the composition of the present invention, the vehicle(s) or a portion of the vehicle(s), are added to the compounding vessel, followed by the remaining excipients and the actives. The mixture is mixed until all solids are dissolved. Additional solvent to bring the composition to final volume may be added if needed. Additives, such as those listed above, may also be included in the vessel and mixed into the formulation (the order of addition is not critical).

The compositions according to the present invention will generally be administered to cattle at from about 1 mg to about 100 mg of the antibacterial per kilogram of body weight per day, and from about 0.5 mg to about 5 mg of flunixin meglumine per kilogram of body weight per day. Preferably the compositions of the present invention will be administered to bovines at from about 20 mg to about 50 mg of the antibacterial per kilogram of body weight. More preferably the dose will be about 40 mg/kg of the antibacterial. Preferably the compositions of the present invention will be administered at from about 1 mg to about 3 mg flunixin meglumine per kilogram of body weight.

The compositions according to the present invention will generally be administered to swine at a dose of from 15 mg to about 100 mg of the antibacterial per kilogram of body weight per day, and from about 0.5 mg to about 5 mg of flunixin meglumine per kilogram of body weight per day. Preferably the compositions of the present invention will be administered to swine at from about 20 mg to about 50 mg of the antibacterial per kilogram of body weight and about 1 mg to about 2 mg of flunixin meglumine per kg of body weight.

The compositions may be administered once daily or divided into multiple doses. Often only one dose will be sufficient to treat the infection. In some circumstances one dose followed by a second dose 48 hours later will be required to treat the animal. The precise dose will depend on the stage and severity of the infection, the susceptibility of the infecting organism to the composition, and the individual characteristics of the animal species being treated, as will be appreciated by one of ordinary skill in the art.

The compositions according to the present invention are particularly useful for cattle and other bovids, swine, and other large mammals. In addition to the treatment of bovine respiratory disease, the compositions of this invention are also suitable for the treatment of infectious diseases associated with inflammation such as swine respiratory disease, footrot, acute mastitis, pinkeye (infectious keratoconjunctivitis), acute pneumonia, metritis and enteritis. The dosage regimen for treatment of such diseases would be as described above.

Mastitis is a complex disease that occurs in lactating females, and is of particular economic importance in dairy cows and goats. Several pathogenic agents may be involved, including *Staphylococcus aureus*, *E. coli*, and *Streptococcus*. The acute form of mastitis has a sudden onset, the udder is enlarged, hot to the touch and tender usually the affected animal will have a fever. If not treated promptly, the udder may be permanently damaged and milk production decreased or lost.

Currently, acute mastitis is treated with antibiotics, antiinflammatories and oxytocin. The use of the formulations of the present invention would be an improvement over presently known methods of treating mastitis because it would combine one of the most effective of the standard treatment combinations into a single, conveniently administered formulation.

Pinkeye is an acute infectious disease of cattle, sheep and other animals that is characterized by inflammation of the tissues of the eye, characterized by inflammation of the tissues of the eye, accompanied by nasal discharge, lacrimation and copious ocular discharge. Affected animals may display extreme discomfort, resulting in a drop in milk production; in extreme cases permanent blindness occurs. The disease, which is caused by *Moraxella bovis* in cattle, is widespread, especially among range and feedlot cattle, and is of great economic importance to the cattle industry.

Currently, pinkeye is treated by administration of various antibiotics. The use of the formulations of the present invention would be an improvement over presently known methods of treating pinkeye because it would provide good antibiotic therapy along with an NSAID to reduce the ocular inflammation.

Footrot (interdigital phlegmon) is an acute infection of the interdigital space that occurs throughout the world in both beef and dairy cattle. *Fusobacterium necrophorum* is the major cause of footrot, although other organisms, including *Bacteroides melaninogenicus*, can be involved. The major symptoms include pain, severe lameness, fever, anorexia, and reduced milk production.

Currently, footrot is treated by antibiotic therapy; recommended therapy can involve treatment for up to five days. The use of the formulations of the present invention for the treatment of footrot would be an improvement over presently known treatments because it would provide the proven efficacy of florfenicol (with fewer administrations), along with an NSAID to reduce the inflammation caused by footrot and make the animal feel better.

The compositions of the present invention are also useful for the prevention of these diseases in animals at high risk of developing those diseases. For example, the presently-claimed compositions can be administered to cattle at high risk of developing bovine respiratory disease at the same dosages recommended for treatment of bovine respiratory disease.

The present invention is more particularly described in the following examples which are intended as illustrative only since numerous modifications and variations therein will be apparent to those skilled in the art.

EXAMPLES

Example 1

Florfenicol/Flunixin Combination Formulations

| Ingredient | Percent (w/v) Formulation 1A Florfenicol 300 mg/ml Flunixin 16.5 mg/ml | Percent (w/v) Formulation 1B Florfenicol 300 mg/ml Flunixin 33 mg/ml |
|---|---|---|
| Florfenicol | 30.0 | 30.0 |
| flunixin meglumine | 2.737 | 5.474 |
| N-methyl-2-pyrrolidone | 25.0 | 25.0 |
| propylene glycol | 15.0 | 15.0 |
| polyethylene glycol 300 | QSAD | QSAD |
| Density | 1.161 g/ml | 1.167 g/ml |

The N-methyl-2-pyrrolidone, propylene glycol and approximately 90% of the PEG 300 required were charged to the compounding vessel and mixed well. The florfenicol and flunixin meglumine were added with mixing until all solids were dissolved. The volume was adjusted with the remaining PEG 300.

Example 2

Pharmacokinetics of Florfenicol in Combination Product

Formulation 1A of Example 1 (SCH 529752) was assessed in a pilot pharmacokinetic study involving 12 cattle in which 6 received florfenicol (NUFLOR) subcutaneously and 6 received Formulation 1A subcutaneously. A dose of 40 mg/kg of florfenicol and a dose of 2.2 mg/kg of flunixin was used. The results are shown in FIG. 1. This preliminary study provided good evidence that the pharmacokinetics of florfenicol, the formulation of the present invention, are very similar to that provided by the already-marketed product, NUFLOR.

Example 3

Pharmacokinetics of Flunixin in Combination Product

In a second study, the pharmacokinetic profile of the second active component in Formulation 1A, flunixin, was examined. The pharmacokinetic profile of flunixin was evaluated following administration to cattle as the approved single entity flunixin meglumine product, FINADYNE, and as the combination product Formulation 1A. This study was conducted in four phases using six cattle (3 males, 3 females). All animals received FINADYNE intravenously (IV) in the first phase. This was followed, after a washout period, by the administration of FINADYNE intramuscularly (IM) to 3 cows and FINADYNE subcutaneously (SQ) to 3 cows. In the next phase the animals were crossed over and received FINADYNE IM or SQ. In the final phase, all six cattle received the flunixin/florfenicol combination product (Formulation 1A). All animals received flunixin at a dose of 2.2 mg/kg, regardless of the formulation or route of administration.

Figure 2:
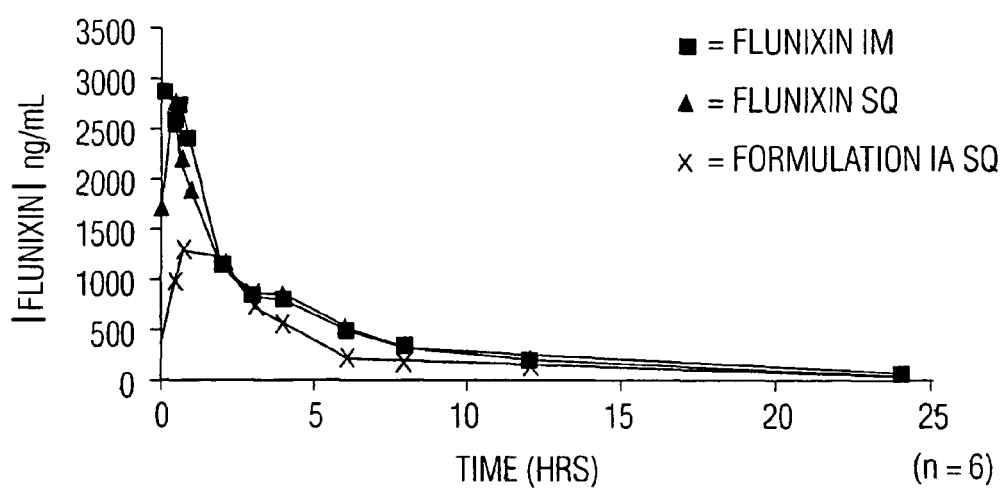
FIG. 2 is a graph showing the mean plasma concentration of flunixin vs. time after parenteral administration of BAN- AMINE/FINADYNE flunixin meglumine or a florfenicol-flunixin meglumine combination composition of the present invention.

Blood samples for determination of flunixin concentration were collected at 0, 0.17, 0.5, 0.75, 1, 2, 3, 4, 6, 8, 12 and 24 hours after dosing. The results are summarized in Table 1 below and in FIG. 2.

TABLE 1

| Route | $C_{max}$ (ng/mL) | $T_{max}$ (hr) | AUC (0-inf) (hr*ug/mL) | F (%) |
|---|---|---|---|---|
| Flunixin IV | — | — | 13.6 | |
| Flunixin IM | 3235 | 0.51 | 10.5 | 78 |
| Flunixin SQ | 2858 | 0.54 | 10.9 | 81 |
| Formulation 1A SQ | 1480 | 1.21 | 6.47 | 48 |

At the final phase of the study, the 6 cattle were given Formulation 1A at a dose of 10 mL per 75 kg SQ (equivalent to 40 mg/kg of florfenicol and 2.2 mg/kg of flunixin). The kinetics of flunixin when administered as Formulation 1A are different from the kinetics of flunixin when administered as FINADYNE. As such, the clinical dose response of Formulation 1A were ascertained in a subsequent study (described below).

Example 4

Clinical Response of Cattle to Flunixin in Combination Product

As the study of Example 3 demonstrated that the bioavailability of flunixin from the combination formulation (Formulation 1A) was lower than the approved single-entity product, FINADYNE, a clinical study was undertaken to compare the clinical response of cattle to flunixin when administered at two different concentrations of flunixin within combination formulations (Formulation 1A and Formulation 1B).

Ninety-six (96) head of cattle demonstrating classic symptoms of bovine respiratory disease were randomly allocated to treatment with one of the following three treatments at a dose of 20 mL/150 kg of body weight (BW):

TABLE 2

| Treatment | Dosage | Route of Administration | Animals/ Treatment |
|---|---|---|---|
| Formulation 1A | 40 mg/kg florfenicol & 2.2 mg/kg flunixin, SID × 1 | SQ | 32 |
| Formulation 1B* | 40 mg/kg florfenicol & 4.4 mg/kg flunixin, SID × 1 | SQ | 32 |
| NUFLOR | 40 mg/kg florfenicol, SID × 1 | SQ | 32 |

*Double the concentration of flunixin in Formulation 1A above

Figure 3:
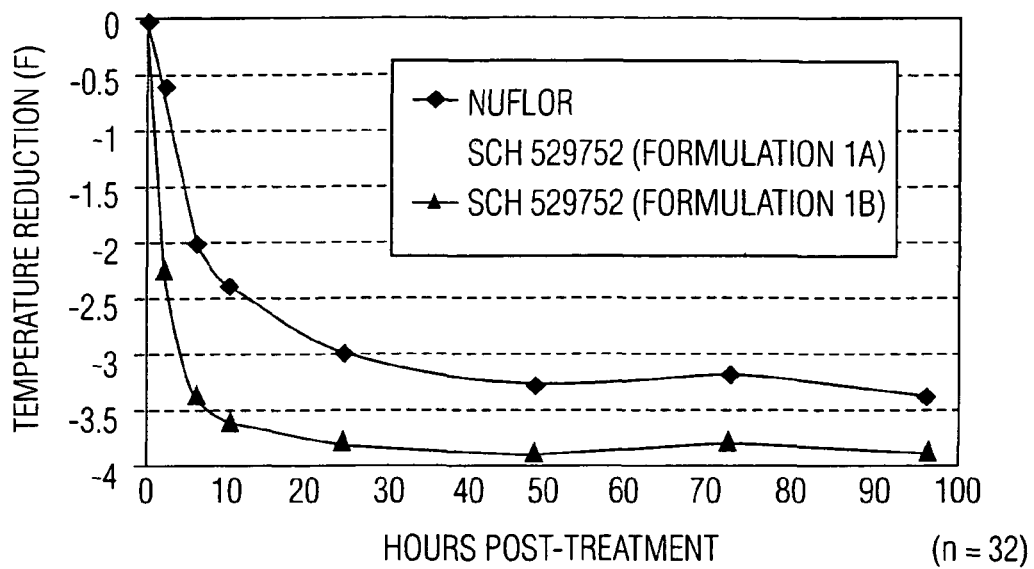
FIG. 3 is a graph showing the effect of flunixin within a florfenicol-flunixin meglumine combination composition of the present invention.

All three treatments were administered subcutaneously once at 40 mg/kg BW of florfenicol (20 mL/150 kg BW). Formulation 1A co-delivered flunixin at a dose of 2.2 mg/kg BW. Formulation 1B co-delivered flunixin at a dose of 4.4 mg/kg BW. Rectal temperature was assessed at various times throughout the study. Results are shown in FIG. 3. The antipyretic response was similar in both treatment groups receiving combination formulations and superior to NUFLOR at all timepoints. It was concluded that there was no incremental benefit to increasing the concentration of flunixin with in the combination formulation.

Example 5

Dose Confirmation Study for Flunixin

The optimal dose of flunixin determined in the study of Example 4 was used in a dose confirmation study. For this study, one-hundred seventy-five (175) beef feeder calves exhibiting clinical signs of acute BRD, were selected. Enrollment was limited to cattle demonstrating the following clinical signs:
  Clinical illness index score of 2 (moderately ill) or 3 (severely ill)
  At least two respiratory characteristics scored as abnormal (polypnea, dyspnea, coughing, mucopurulent nasal discharge)
  Pyrexia ≧ 104.5° F.
Upon enrollment the cattle were randomly allocated to one of 3 treatment groups:

TABLE 3

| Treatment | Dosage | Route of Administration | Animals/ Treatment |
|---|---|---|---|
| Formulation 1A | 40 mg/kg florfenicol & 2.2 mg/kg flunixin, SID × 1 | SQ | 26 |
| NUFLOR + FINADYNE | 40 mg/kg florfenicol & 2.2 mg/kg flunixin, SID × 1 | SQ (NUFLOR) and IV (FINADYNE) | 30 |
| NUFLOR | 40 mg/kg florfenicol, SID × 1 | SQ | 30 |

The objective of this study was to compare the treatment response to a combination formulation of the present invention relative to an approved positive control (FINADYNE and NUFLOR, each given by their approved route of administration) and negative (NUFLOR alone) control. Efficacy was assessed by scoring of clinical symptoms, rectal temperature and total lung consolidation.

After enrollment and treatment on Day 0, the calves had their rectal temperatures taken at approximately 2, 6 and 10 hours post-treatment. Calves were then clinically scored once daily on Days 1, 2, 3 and 4; rectal temperatures were taken once daily after the animal's morning observation.

Treatment success was assessed on Study Day 4. An animal was classified as a treatment success if the animal had a rectal temperature of ≦103.5° F., a clinical illness index score ≦1 (slightly ill) and normal respiratory character (less than two abnormal scores for polypnea, dyspnea, coughing and mucopurulent nasal discharge).

Lastly, on Day 4 the calves were humanely euthanized for necropsy and evaluation of pneumonic lesions/lung consolidation. Percent lung consolidation was calculated based on visual and palpation scores of 0, 1, 5, 10, 20, 30, 40, 50, 60, 70, 80, 90 or 100% assigned to each of the eight lung lobes. The overall lung consolidation is then calculated using a standard formula (see Shaw, et al., DISEASES OF SWINE, 8$^{th}$ Ed. 914 (ISU Press, 1999).

Figure 4:
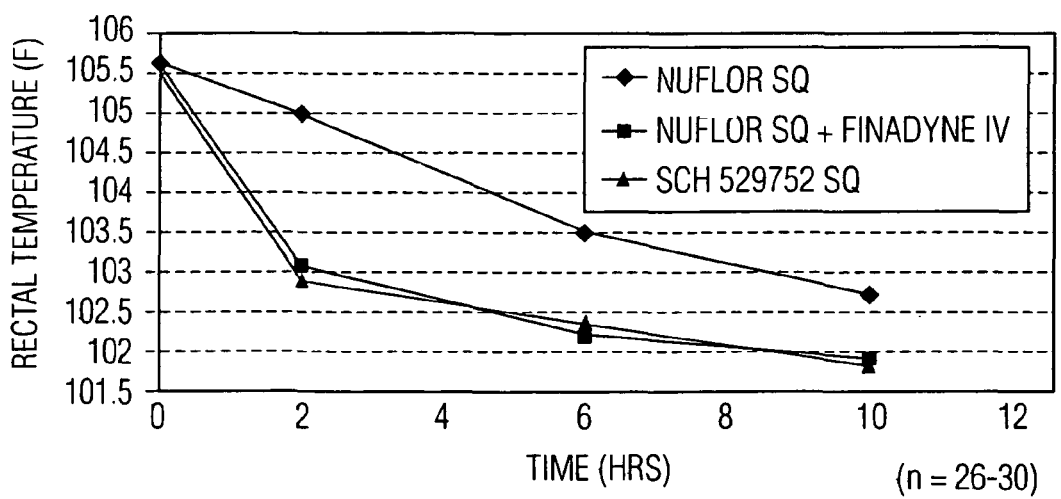
FIG. 4 is a graph showing the effect of treatment with a florfenicol-flunixin meglumine combination composition of the present invention on antipyretic response in cattle with BRD.
Figure 5:
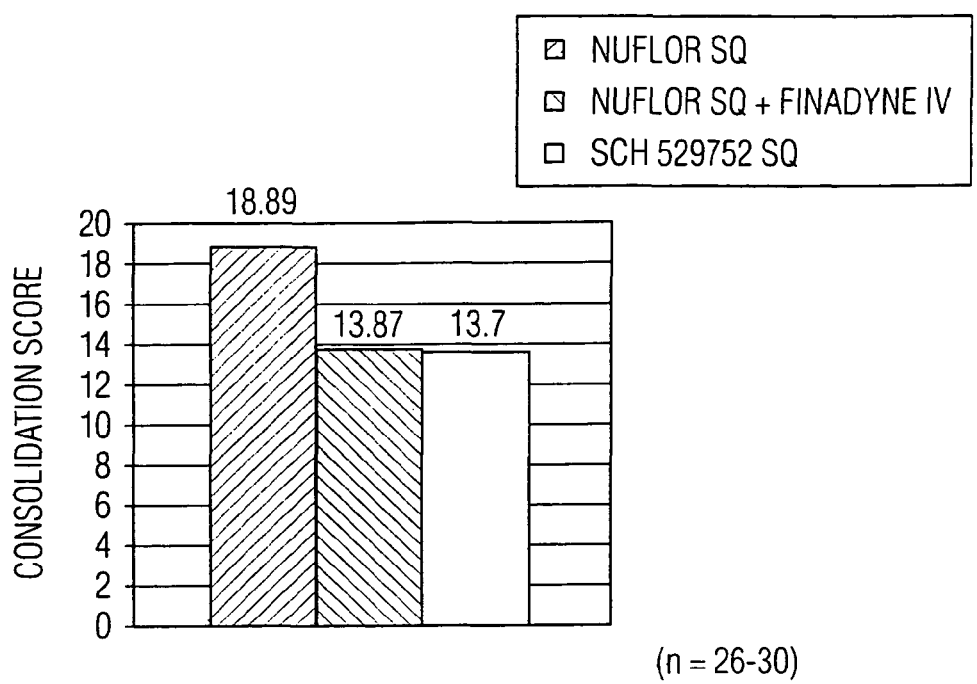
FIG. 5 is a graph showing the effect of treatment with a florfenicol-flunixin meglumine combination composition of the present invention on lung consolidation score.
Figure 6:
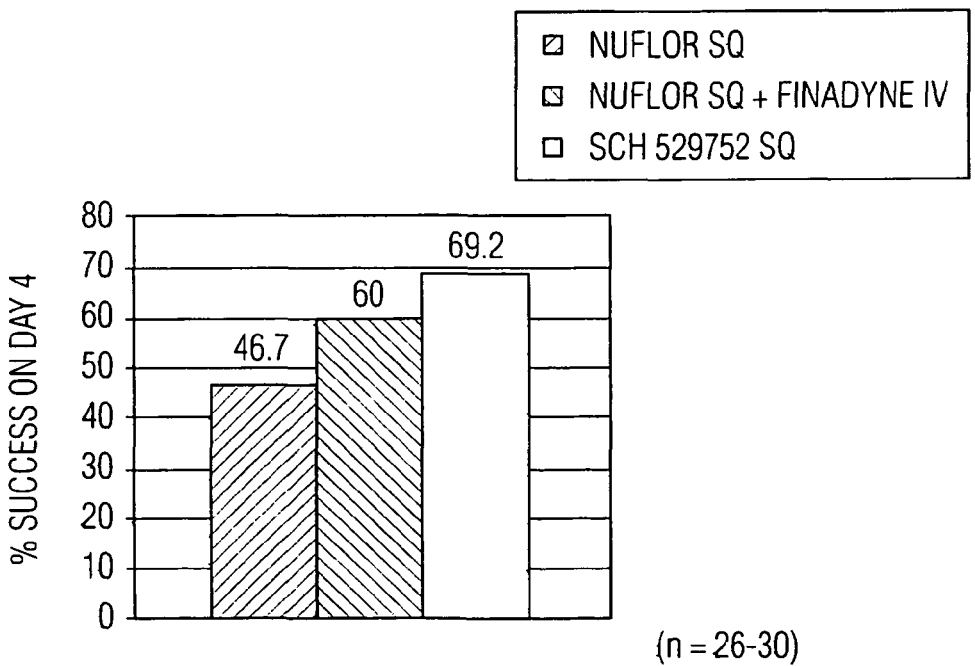
FIG. 6 is a graph showing the effect of treatment with a florfenicol-flunixin meglumine combination composition of the present invention on the clinical success rate.

Results from this study are summarized in FIGS. 4, 5 and 6.

The addition of flunixin to treatment resulted in a more rapid decrease in rectal temperature ($p<0.001$ at 2, 6 and 10 hours post-treatment) relative to administration with florfenicol alone. The response was the same whether the flunixin is administered in a separate syringe and given IV or co-administered within a subcutaneous injection of Formulation 1A (see FIG. 4).

The addition of flunixin to treatment resulted in numerically less lung consolidation ($p=0.08$ [Formulation 1A vs. NUFLOR], $p=0.1$ [NUFLOR+FINADYNE vs. NUFLOR]). The response is the same whether the flunixin is administered in a separate syringe and given IV (FINADYNE) or co-administered within a subcutaneous injection of Formulation 1A (see FIG. 5).

As shown in FIG. 6, the addition of flunixin numerically improved the rate of success ($p=0.1$ [Formulation 1A vs. NUFLOR], $p=0.3$ [NUFLOR+FINADYNE vs. NUFLOR]).

Example 6

Florfenicol/Flunixin Combination Formulations

| Ingredient | Percent (w/v) | | | |
|---|---|---|---|---|
| florfenicol | 30.0 | 30.0 | 50.0 | 20.0 |
| flunixin meglumine | 2.74 | 2.7 | 4.6 | 1.8 |
| N-methyl-2-pyrrolidone (NMP) | 25.0 | — | — | — |
| citric acid | 1.0 | — | — | — |
| propylene glycol | 15.0 | — | — | — |
| dimethylacetamide | — | 11.9 | 30.0 | — |
| glycerol formal | — | QS | QS | QS |
| polyethylene glycol (PEG) 300 | QS | — | — | — |

The NMP or dimethylacetamide, citric acid, propylene glycol, and approximately 90% of the PEG 300 or glycerol formal required for each formulation were charged to the compounding vessel and mixed well. The florfenicol and flunixin meglumine were added with mixing until all solids were dissolved. The volume was adjusted with the remaining PEG 300 or glycerol formal.

Example 7

Florfenicol/Flunixin Combination Formulations

| Ingredient | Quantity |
| --- | --- |
| florfenicol | 200 mg/ml |
| flunixin meglumine | 16.5 mg/ml |
| methyl p-hydroxybenzoate | 1 mg/ml |
| propyl p-hydroxybenzoate | 0.1 mg/ml |
| N-methyl-2-pyrrolidone (NMP) | 250 mg/ml |
| water | 0.15 ml |
| polyethylene glycol 200 | QS |

The NMP and a portion of the polyethylene glycol 200 are charged to the compounding vessel. Florfenicol, methyl p-hydroxybenzoate and propyl p-hydroxybenzoate are added to the vessel and mixed until dissolved. Water is added, followed by the flunixin meglumine, and mixed until solids are dissolved. Q.S. to final volume with polyethylene glycol 200 if needed.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. A composition for the treatment of microbial infection in an animal, consisting of about 300 mg/ml of florfenicol, about 16.5 to about 33.0 mg/ml of flunixin and/or a pharmaceutically acceptable salt of flunixin, triacetin, 2-pyrrolindone and other inert ingredients wherein the inert ingredients are selected from the group consisting of preservatives, chelating agents, antioxidants, and stabilizers.

* * * * *